(12) United States Patent
Douglas et al.

(10) Patent No.: US 11,202,061 B1
(45) Date of Patent: Dec. 14, 2021

(54) ILLUSTRATING DIRECTION OF BLOOD FLOW VIA POINTERS

(71) Applicants: Robert Douglas, Winter Park, FL (US); David Douglas, Winter Park, FL (US)

(72) Inventors: Robert Douglas, Winter Park, FL (US); David Douglas, Winter Park, FL (US)

(*) Notice: Subject to any disclaimer, the term of this patent is extended or adjusted under 35 U.S.C. 154(b) by 3 days.

(21) Appl. No.: 16/506,073

(22) Filed: Jul. 9, 2019

Related U.S. Application Data

(63) Continuation-in-part of application No. 15/878,463, filed on Jan. 24, 2018, now Pat. No. 10,795,457, which is a continuation-in-part of application No. 14/877,442, filed on Oct. 7, 2015, now Pat. No. 9,980,691, which is a continuation-in-part of application No. 12/176,569, filed on Jul. 21, 2008, now Pat. No. 9,349,183, which is a continuation-in-part of application No. 11/941,578, filed on Nov. 16, 2007, now Pat. No. 8,384,771.

(60) Provisional application No. 60/877,931, filed on Dec. 28, 2006.

(51) Int. Cl.
*H04N 7/18* (2006.01)
*H04N 13/344* (2018.01)
*A61B 5/00* (2006.01)
*H04N 13/183* (2018.01)

(52) U.S. Cl.
CPC ........... *H04N 13/344* (2018.05); *A61B 5/489* (2013.01); *H04N 13/183* (2018.05)

(58) Field of Classification Search
CPC .................................................. H04N 13/344
USPC ............................................................ 348/53
See application file for complete search history.

(56) References Cited

U.S. PATENT DOCUMENTS

| 5,535,747 | A  | * | 7/1996  | Katakura  | A61B 8/04     |
|           |    |   |         |           | 600/438       |
| 6,847,336 | B1 | * | 1/2005  | Lemelson  | A61B 1/00048  |
|           |    |   |         |           | 345/8         |
| 8,384,771 | B1 | * | 2/2013  | Douglas   | G02B 27/017   |
|           |    |   |         |           | 348/53        |
| 9,349,183 | B1 | * | 5/2016  | Douglas   | G06T 7/593    |
| 2005/0168461 | A1 | * | 8/2005  | Acosta    | G06T 15/08    |
|           |    |   |         |           | 345/419       |
| 2006/0181482 | A1 | * | 8/2006  | Iaquinto  | A61B 6/00     |
|           |    |   |         |           | 345/8         |
| 2006/0241458 | A1 | * | 10/2006 | Hayashi   | A61B 8/06     |
|           |    |   |         |           | 600/453       |
| 2007/0263915 | A1 | * | 11/2007 | Mashiach  | G06K 9/342    |
|           |    |   |         |           | 382/130       |
| 2010/0081912 | A1 | * | 4/2010  | McKenna   | A61B 5/0097   |
|           |    |   |         |           | 600/368       |
| 2011/0196237 | A1 | * | 8/2011  | Pelissier | A61B 8/06     |
|           |    |   |         |           | 600/454       |
| 2014/0307067 | A1 | * | 10/2014 | Douglas   | H04N 13/363   |
|           |    |   |         |           | 348/53        |

(Continued)

*Primary Examiner* — Leron Beck

(57) ABSTRACT

Pointers are added to a 3D volumetric dataset to help the user visualize the direction of blood flow. A 3D volume containing at least one blood vessel is created. Next, the direction of the blood flow is determined. Next, at least pointer is placed into the 3D volume in an aligned fashion with the direction of blood flow such that the 3D volume is modified. Next, the modified 3D volume is displayed on a head display unit, such as an augmented reality or virtual reality display. Next, at least one pointer is advanced to a new position for additional modification of the 3D imaging volume.

16 Claims, 6 Drawing Sheets

(56) References Cited

U.S. PATENT DOCUMENTS

2015/0379351 A1* 12/2015 Dibenedetto ...... G06K 9/00671
345/633

* cited by examiner

ILLUSTRATING DIRECTION OF BLOOD FLOW VIA POINTERS

TECHNICAL FIELD

Aspects of this disclosure are generally related to radiological imaging, and more particularly to blood vessel appearance using extended reality headsets.

BACKGROUND

One of the challenges that physicians face when viewing a volume with an augmented reality, virtual reality or mixed reality headset is visualization of blood flow.

SUMMARY

All examples, aspects and features mentioned in this document can be combined in any technically possible way.

In accordance with some implementations a method of denoting blood flow within a 3D volume on a head display unit (HDU), comprises: generating a 3D volumetric dataset containing at least one blood vessel; generating at least one pointer; determining the direction of blood flow; modifying the 3D volumetric dataset by placing the at least one pointer in proximity to the at least one blood vessel in a direction aligned with a direction of blood flow; displaying, in said HDU, a left eye image based on said modified 3D volumetric dataset and a right eye image based on said modified 3D volumetric dataset, wherein said left eye image and said right eye image are alternate three-dimensional images; and displaying, in said HDU, the at least one pointer advancing in the direction of blood flow. In some implementations placing the at least one pointer in proximity to the at least one blood vessel comprises placing a 2D arrow. In some implementations placing the at least one pointer in proximity to the at least one blood vessel comprises placing a 3D arrow. Some implementations comprise displaying, in said HDU, the pointer with changing color. Some implementations comprise displaying, in said HDU, the pointer advancing in the direction of blood flow faster in arteries than veins.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
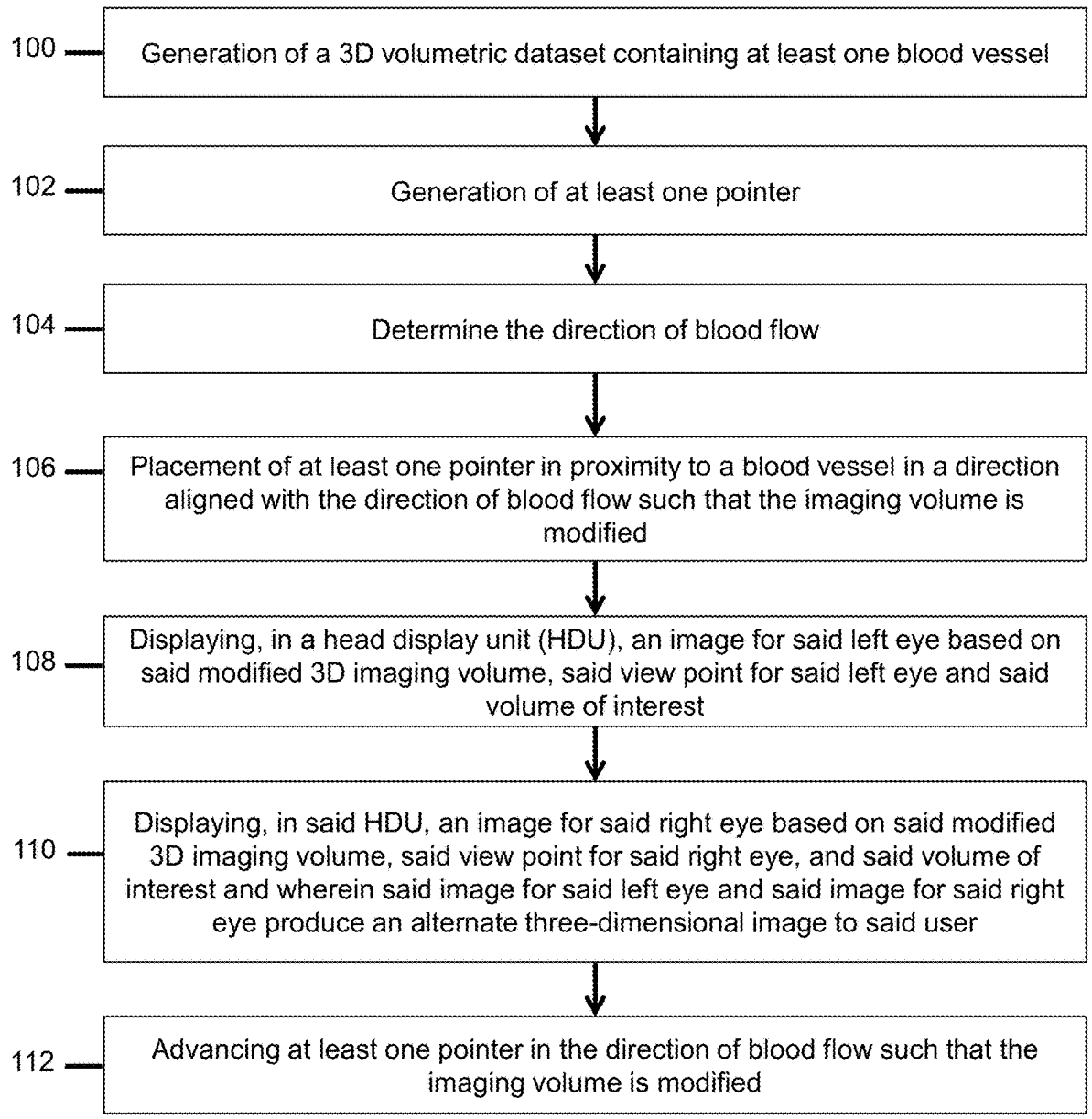
FIG. 1 illustrates the method for using pointers to denote blood flow direction within a 3D volumetric dataset and viewing with a head display unit.

FIG. 1 illustrates an implementation of a method for using pointers to denote blood flow direction within a 3D volumetric dataset and viewing with a head display unit. In the first step 100, a 3D volumetric dataset containing at least one blood vessel is generated. In the second step 102, at least one pointer is generated. In the third step 104, the direction of blood flow is determined. In the fourth step 106, at least one pointer in proximity to a blood vessel in a direction aligned with the direction of blood flow is placed such that the 3D volumetric dataset is modified. In the fifth step 108, an image for said left eye based on said modified 3D imaging volume, said view point for said left eye and said volume of interest is displayed, in the left eye display of the said HDU. In the sixth step 110, an image for said right eye based on said modified 3D imaging volume, said view point for said right eye, and said volume of interest and wherein said image for said left eye and said image for said right eye produce an alternate three-dimensional image to said user. In the seventh step 112, at least point pointer is advanced in the direction of blood flow such that the imaging volume is modified. Some portions of this process can be repeated such that multiple modified 3D imaging volumes are created and displayed on the HDU. This would serve to provide the visualization of moving arrows and help the imager better understand blood flow.

Figure 2:
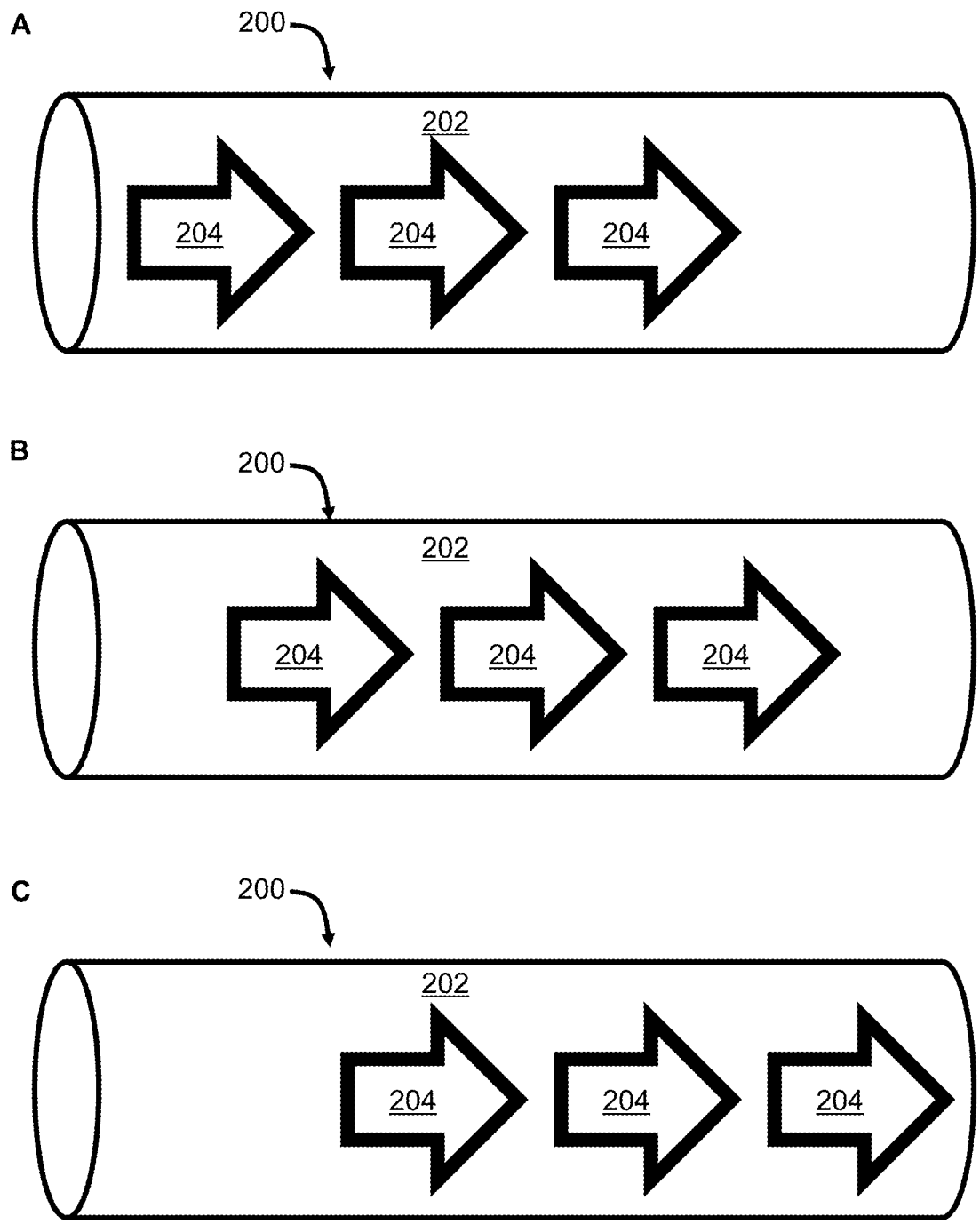
FIG. 2 illustrates advancing pointers to depict the direction of the blood flow.

FIG. 2 illustrates advancing pointers (or arrows) to depict the direction of the blood flow. In the human body, it is common for blood in most arteries to be directed away from the heart and for blood in most veins to be directed towards the heart. However, in some situations in the body (e.g., subclavian steal with retrograde flow in the vertebral artery), this rule does not apply. It can be difficult for even an experienced imager to readily determine which structures are arteries and which structures are veins. Additionally, even if an imager is able to identify a structure as an artery, it can be difficult to determine its orientation without carefully tracing it back to its origin. Through advances in computer processing, these vessels and the direction of blood flow therein can be determined. An effective visual representation method is required. In this method, advancing pointers along an artery can be performed to indicate the direction of blood flow. Similarly, advancing pointers can be performed in a vein. The color of the pointers can be changed to designate to the user whether it is an artery or vein. Further, the rate of advance of the pointers can also be varied, such as to match the natural blood flow rate for a realistic understanding of the hemodynamics of the patient. The pointers could be located in close proximity to (or within the blood vessels, such as within the center of the blood vessel). As a blood vessel curves through the 3D volume space, the path of the pointers would also curve to match that of the normal blood flow. In FIG. 2A, the pointers 204 are shown within the blood vessel lumen 202 in an initial position with respect to the blood vessel wall 200 and position of the remainder of structures within the imaging volume, which are not shown. This would represent the appearance of the imaging volume at an initial time point. In FIG. 2B, the pointers 204 are shown within the blood vessel lumen 202 in an second, slightly advanced position with respect to the blood vessel wall 200 and position of the remainder of structures within the imaging volume, which are not shown. This would represent the appearance of the imaging volume at a subsequent time point. In FIG. 2C, the pointers 204 are shown within the blood vessel lumen 202 in an third, even further advanced position with respect to the blood vessel wall 200 and position of the remainder of structures within the imaging volume, which are not shown. This would represent the appearance of the imaging volume at an additional subsequent time point. The volume that would displayed to the user on an extended reality (i.e., augmented reality, mixed reality or virtual reality headset) would therefore be dynamic and change over time. Even if the user were looking at a particular structure without moving his or her head, some items within the 3D volume would appear to be moving.

Figure 3:
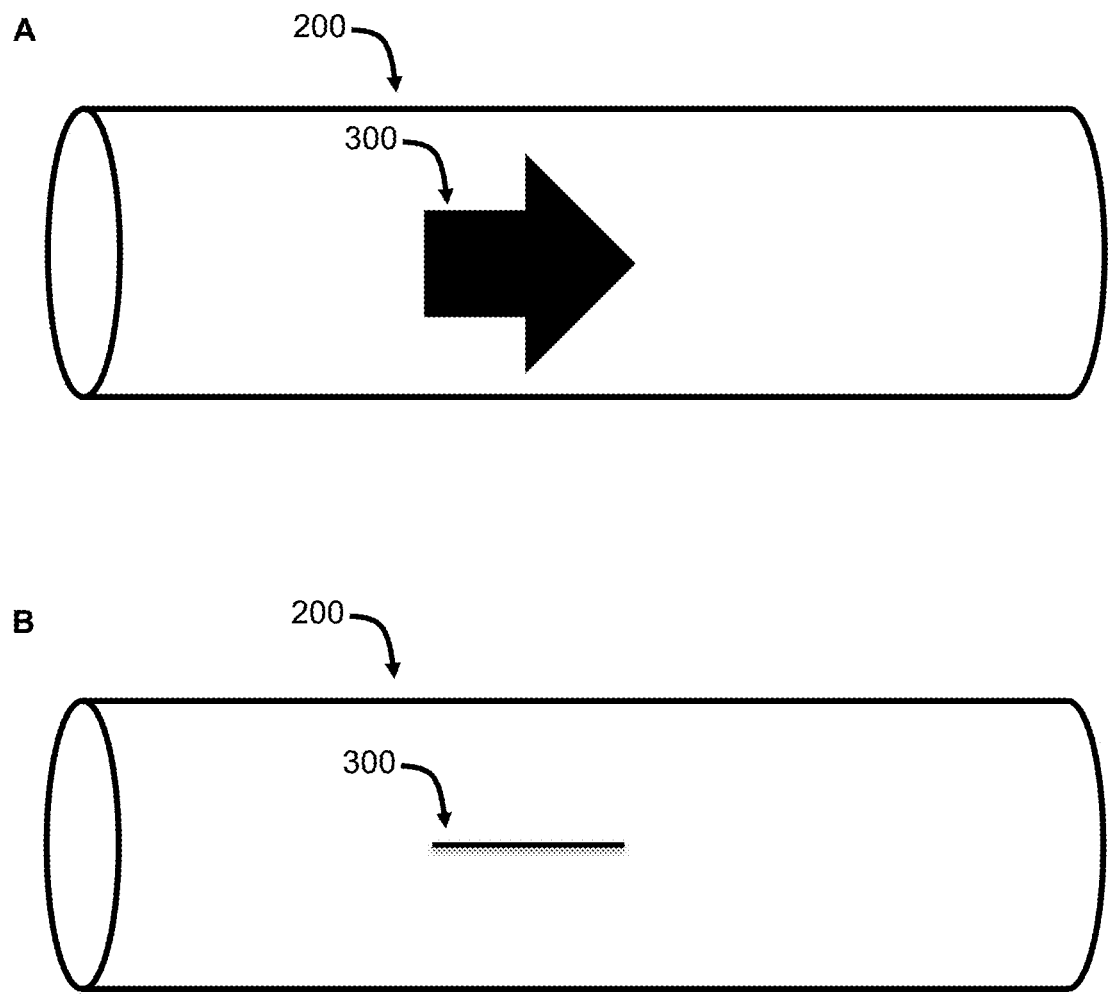
FIG. 3 illustrates placement of a 2D pointer into the 3D volume.

FIG. 3 illustrates placement of a 2D pointer into the 3D volume. In FIG. 3A, a 2D pointer 300 is placed into the blood vessel 200 within the 3D imaging volume. Note that this image illustrates a side view wherein the user's left and right eye view points and left and right eye viewing angles show the side of the 2D pointer 300 and the side of the blood vessel 200 within the 3D volume. In FIG. 3B, the 2D pointer 300 is placed into the blood vessel 200 within the 3D volume. Note that this image illustrates a top down view wherein the user's left and right eye view points and left and right eye viewing angles show the 2D pointer 300 and the top of the blood vessel 200 within the 3D volume. Note that since the 2D pointer is a planar slice, it nearly disappears when viewing from a near top position. A true top position with a planar 2D slice would completely disappear unless the 2D arrow was reoriented. Non-planar slices could also be used, which would be seen from any viewing angle and could be beneficial for viewing direction of blood on a curved vessel.

Figure 4:
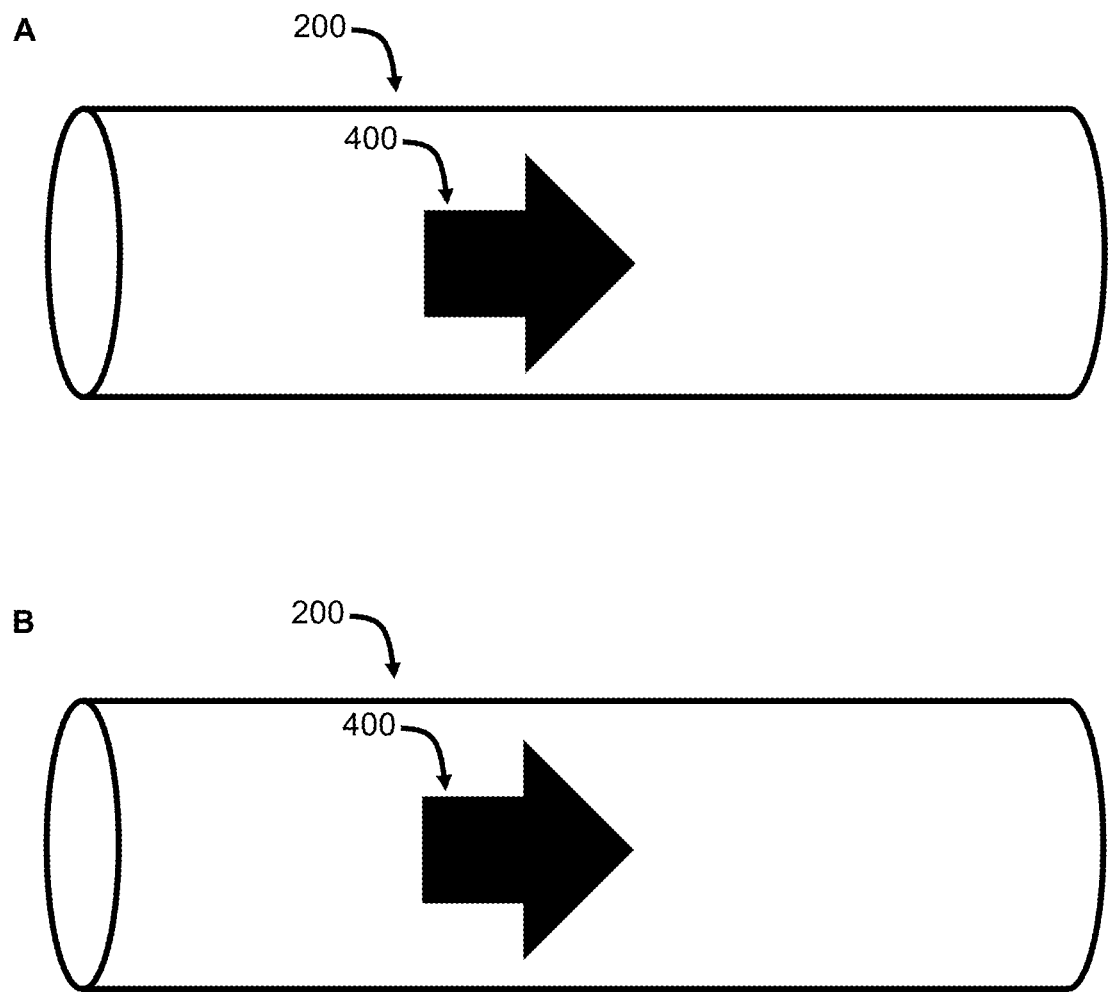
FIG. 4 illustrates placement of a 3D pointer into the 3D volume.

FIG. 4 illustrates placement of a 3D pointer into the 3D volume. In FIG. 4A, a 3D pointer 400 is placed into the blood vessel 200 within the 3D imaging volume. Note that this image illustrates a side view wherein the user's left and right eye view points and left and right eye viewing angles show the side of the 3D pointer 400 and the side of the blood vessel 200 within the 3D volume. In FIG. 4B, the 3D pointer 400 is placed into the blood vessel 200 within the 3D volume. Note that this image illustrates a top down view wherein the user's left and right eye view points and left and right eye viewing angles show the 3D pointer 400 and the top of the blood vessel 200 within the 3D volume. Note that since the pointer is 3D, it is clearly visualized when viewing from a near top position. Such a pointer could be constructed by arranging a series of 2D non-planar slices to form a cone abutting a cylinder (also made of combination of planar and non-planar slices) yielding a 3D pointer 400. By inserting this into the 3D volume, the volume would be modified.

Figure 5:
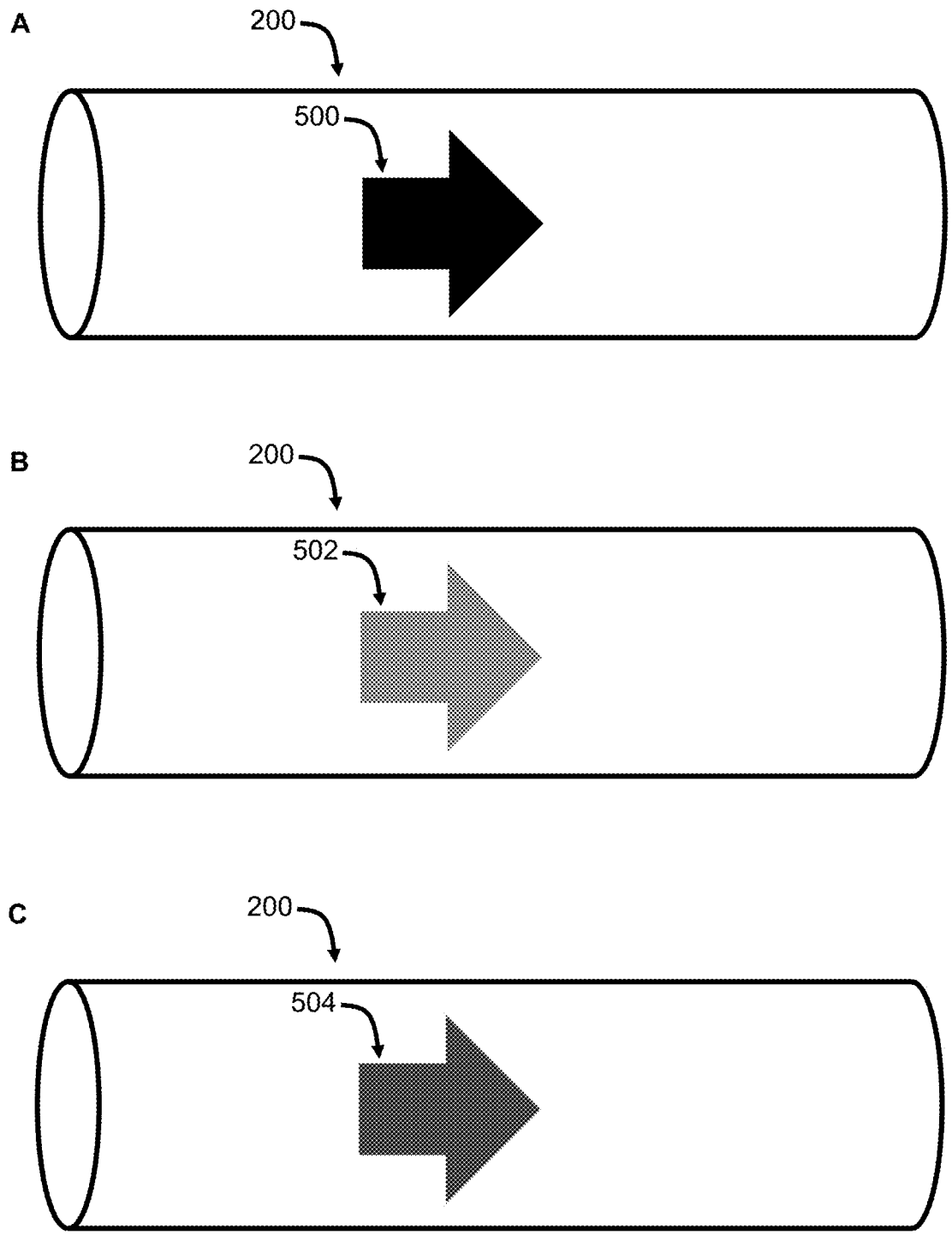
FIG. 5 illustrates placement of a 3D pointer into the 3D volume wherein the appearance of the 3D pointer can be modified.

FIG. 5 illustrates placement of a 3D pointer into the 3D volume wherein the appearance of the 3D pointer can be modified. In FIG. 5A, a 3D pointer 500 is placed into the blood vessel 200 within the 3D volume. Note that the appearance of the 3D pointer 500 is black. In FIG. 5B, the 3D pointer 502 is placed into the blood vessel 200 within the 3D volume. Note that the appearance of the 3D pointer 502 is gray. In FIG. 5C, a 3D pointer 504 is placed into the blood vessel 200 within the 3D volume. Note that the appearance of the 3D pointer 504 is red. Note that the appearance of the pointer can vary. It can be 2D or 3D. It can be a wide range of colors. It can be a wide range of shapes. It can have a wide range of textures.

Figure 6:
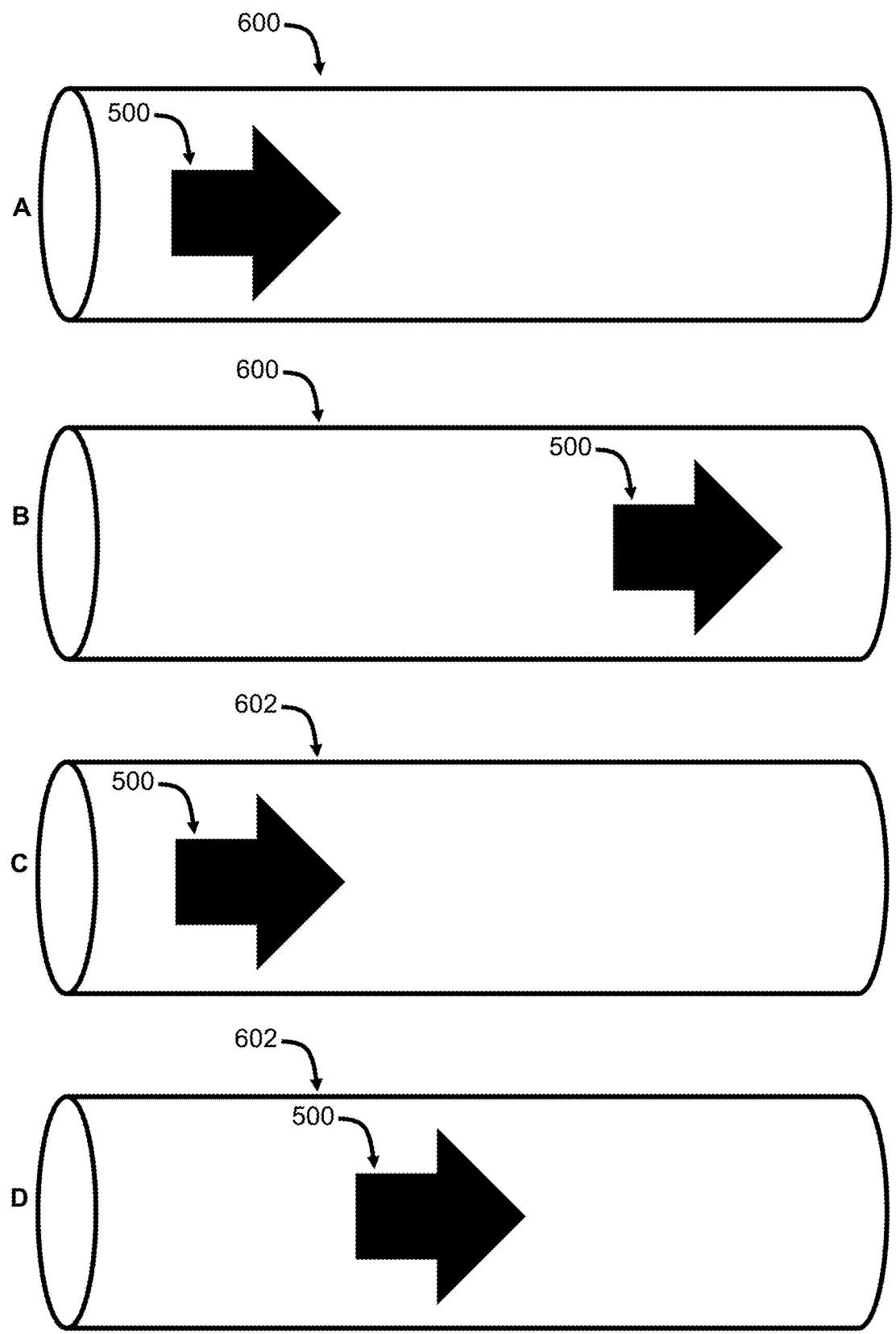
FIG. 6 illustrates variable pointer rates of movement.

FIG. 6 illustrates variable pointer rates of movement. In FIG. 6A, the black 3D pointer 500 is located within the proximal portion of an artery 600 at time point=x. In FIG. 6B, the black 3D pointer 500 has moved and is located distally towards the end of the artery 600 at time point=x+n. In FIG. 6C, the pointer 500 is located within the distal portion of a vein 602 at time point=x. In FIG. 6D, the pointer 500 is located with the mid portion of the vein 602 at time point=x+n. Note that the 3D pointer 500 is moving faster in the artery 600 as compared to the vein 602.

Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method of denoting blood flow within a 3D volume on a head display unit (HDU), comprising:
   generating a 3D volumetric dataset comprising at least one blood vessel;
   generating at least one pointer;
   determining the direction of blood flow within the at least one blood vessel;
   modifying the 3D volumetric dataset by placing the at least one pointer in proximity to the at least one blood vessel in a direction aligned with the direction of blood flow of the at least one blood vessel to create a first modified 3D volumetric dataset comprising the at least one blood vessel and a first position(s) of the at least one pointer;
   displaying at a first time point, x, in said HDU, a first left eye image based on a left eye view point at the first time point, x, a left eye viewing angle at the first time point, x, and the first modified 3D volumetric dataset including the at least one blood vessel and a first position(s) of the at least one pointer, and a first right eye image based on a right eye view point at the first time point, x, a right eye viewing angle at the first time point, x, and the modified 3D volumetric including the at least one blood vessel and a first position(s) of the at least one pointer, wherein a user viewing the first left eye image and the first right eye image in said HDU sees a first three-dimensional image of the first modified 3D volumetric dataset including the at least one blood vessel and a first position(s) of the at least one pointer;
   modifying the first modified 3D volumetric dataset including a first position(s) of the at least one pointer and the at least one blood vessel by moving the at least one pointer in proximity to the at least one blood vessel in a direction aligned with the direction of blood flow of the at least one blood vessel to create a second modified 3D volumetric dataset including the at least one blood vessel and a second position(s) of the at least one pointer;
   displaying at a second time point, x+n, in said HDU, a second left eye image based on a left eye view point at the second time point, x+n, a left eye viewing angle at the second time point, x+n, and the second modified 3D volumetric dataset including the at least one blood vessel and a second position(s) of the at least one pointer, and a second right eye image based on a right eye view point at the second time point, x+n, a right eye viewing angle at the second time point, x+n, and the modified 3D volumetric dataset including the at least one blood vessel and a second position(s) of the at least one pointer, wherein a user viewing the second left eye image and the second right eye image in said HDU sees a second three-dimensional image of the second modified 3D volumetric dataset including the at least one blood vessel and a second position(s) of the at least one pointer wherein:

the HDU displays dynamic images denoting blood flow within a 3D volume even if the user is not moving his or her head.

2. The method of claim 1 wherein placing the at least one pointer in proximity to the at least one blood vessel comprises placing a 2D arrow.

3. The method of claim 1 wherein placing the at least one pointer in proximity to the at least one blood vessel comprises placing a 3D arrow.

4. The method of claim 1 comprising displaying the pointer with changing colors.

5. The method of claim 1 comprising displaying the pointer advancing in the direction of blood flow faster in arteries than veins.

6. The method of claim 1 further comprising wherein a 3D pointer constructed by arranging 2D non-planar slices to form a cone and arranging 2D non-planar slices to form a cylinder wherein the cone and the cylinder fit together to form a 3D pointer.

7. The method of claim 1 further comprising wherein a 2D arrow is constructed via a single 2D planar slice.

8. The method of claim 1 further comprising wherein a 2D arrow is constructed via a single 2D non-planar slice.

9. The method of claim 1 further comprising wherein the appearance of the 2D arrow changes based on changing viewing position.

10. The method of claim 1 further comprising wherein a 2D pointer moves in a 3D volume, such that the 3D volume is modified.

11. The method of claim 1 further comprising wherein a 3D pointer moves in a 3D volume, such that the 3D volume is modified.

12. The method of claim 1 further comprising wherein a 2D pointer moves in a 3D volume, wherein the location of the 2D pointer is in close proximity to within the blood vessel, but not within the center of the blood vessel.

13. The method of claim 1 further comprising wherein a 3D pointer moves in a 3D volume, wherein the location of the 3D pointer is in close proximity to within the blood vessel, but not within the center of the blood vessel.

14. The method of claim 1 further comprising wherein the pointer moves in a three-dimensional path through the volumetric dataset along the vascular structure.

15. The method of claim 1 further comprising wherein the changing the orientation of the viewing angle changes the appearance of the 2D arrow type pointer.

16. The method of claim 1 further comprising wherein the changing the orientation of the viewing angle changes the appearance of the 3D arrow type pointer.

* * * * *